United States Patent [19]

Grendahl

[11] Patent Number: 5,213,721

[45] Date of Patent: May 25, 1993

[54] PROCESS OF MAKING A MEMBER WITH HOLES

[76] Inventor: Dennis T. Grendahl, 2070 Shoreline Dr., Orono, Minn. 55391

[21] Appl. No.: 632,334

[22] Filed: Dec. 21, 1990

Related U.S. Application Data

[63] Continuation of Ser. No. 419,278, Oct. 10, 1989, abandoned.

[51] Int. Cl.⁵ .............................................. B29D 11/00
[52] U.S. Cl. .................................... 264/1.7; 264/145; 156/155; 156/229; 156/250; 156/264; 156/296
[58] Field of Search .............................. 264/1.7, 145; 351/160 H, 160 R, 154; 156/155, 160, 229, 296, 250, 264; 29/424

[56] References Cited

U.S. PATENT DOCUMENTS

| | | | |
|---|---|---|---|
| 3,899,315 | 8/1975 | Siegmund | 156/155 |
| 4,065,046 | 12/1977 | Roberts et al. | 156/264 |
| 4,127,398 | 11/1978 | Singer, Jr. | 156/296 |
| 4,157,213 | 6/1979 | Phillips | 351/168 |
| 4,624,669 | 11/1986 | Grendahl | 623/5 |
| 4,862,575 | 9/1989 | Shirai et al. | 29/424 |

*Primary Examiner*—Allan R. Kuhns
*Attorney, Agent, or Firm*—Grady J. Frenchick

[57] ABSTRACT

Member of polymethylmethacrylate, polysulfone, polymer or a like material with a plurality of holes arranged in a predetermined, geometrical configuration. The holes are derived at through a procedure of repetitive drawing. Prior to the first drawing operation, each of the holes is filled with a material which is soluble to a certain chemical, yet drawable along with the base material. The member of material can be square, drawn to a reduced cross-sectional area as a square, the reduced cross-sectional members positioned with respect to each other and drawn again in a further operation, and repeated accordingly so that the cross-sectional area of each hole is reduced in proportion to each drawing step. Dependent upon the final drawing step, a subsequent member is provided which includes holes of a significantly reduced cross-sectional area. The member can be utilized as either a contact lens, an intracorneal inlay, an intraocular lens, a medical filter, or a like structure with small holes.

2 Claims, 7 Drawing Sheets

PROCESS FOR DRAWING SECOND GENERATION BOULE

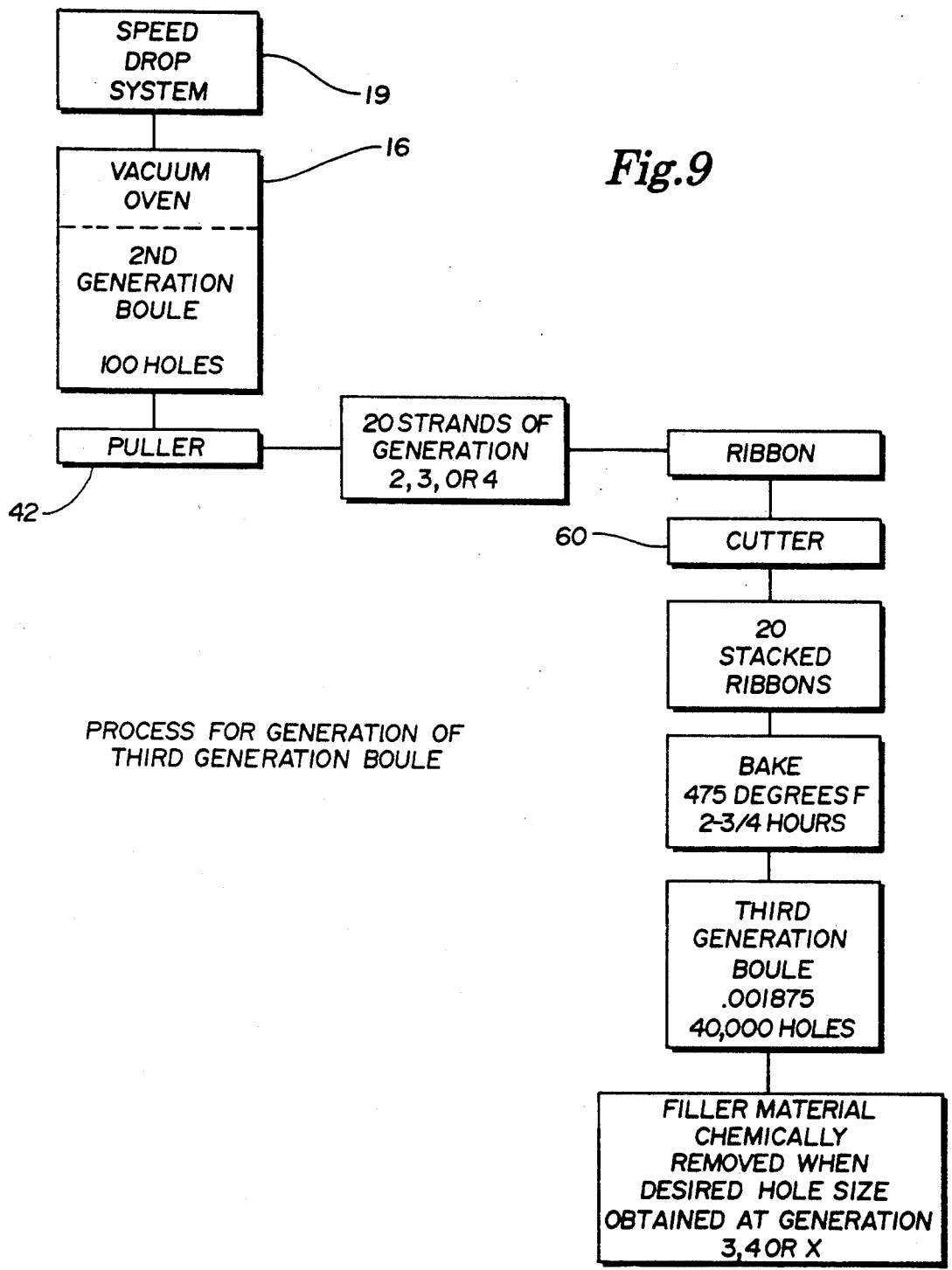

PROCESS OF MAKING A MEMBER WITH HOLES

This is a continuation of co-pending application Ser. No. 07/419,278 filed on Oct. 10, 1989, now abandoned.

BACKGROUND OF THE INVENTION

1. Field of the Invention

The present invention pertains to a member with holes, such as polymethylmethacrylate, polycarbonate, or polysulfone member, and the process of drawing the member with the hole in repetitive steps to reduce the diameter of the holes.

2. Description of the Prior Art

It is of particular benefit to provide members with the smallest possible holes for use in medical applications, as well as other applications. There have been methods to provide holes, such as through machining technology, laser technology or electron beam technology, but the holes have not been the minute dimensions required for some medical applications. The prior art methods have not been satisfactory in providing clean, consistent holes in material, such as PMMA or polysulfone for medical or other scientific applications.

The present invention overcomes the disadvantages of the prior art by providing a process for providing holes in a member through a series of repetitive drawing steps where the holes can be as small as desired with placed in the members predetermined.

SUMMARY OF THE INVENTION

The general purpose of the present invention is to provide a member with very small holes in the order of angstroms per diameter of each hole in polymethylmethacrylate, polysulfone, or other like materials which are drawable. By repeat of drawing steps, the holes can be drawn down to an infinitesimal size. The holes can provide for the passing of fluids or nutrients for example, such as in intracorneal lenses.

According to one embodiment of the present invention there is provided a process of providing holes in a geometrical member, including the steps of forming a geometrical boule member of a predetermined geometrical configuration of a drawable first material, then providing a plurality of holes along a longitudinal axis of the boule member. Each of the holes is filled with a second material which is removable at a later time, and the second material has the same drawing capabilities as the first material of the boule, so that drawing the member with the filled holes decreases the cross-sectional area of the boule into a square strand of material. Then, sections of the drawn material are positioned forming a ribbon, which are baked and placed in a square boule, and a subsequent drawing step occurs again drawing the positioned sections into a decreased cross-sectional area. The step of the continued placement of drawn bundles with respect to each other and continually repeating the drawing step of the drawn bundles reduces the cross-sectional area of each of the holes. Once the desired diameter of each hole is reached, then the drawn member can be formed into any particular shape, such as a circle for an intraocular lens, or the other application. Then, the material filling each of the holes can be dissolved out and cleaned out with appropriate solvent dissolving removal steps and washing steps. In the alternative, the holes can be refilled under heat and pressure with a different material for further processing. The resultant product is a member with very small holes of extremely reduced cross-sectional area which is proportional to the number of drawing steps, as well as other factors related to drawing of the member.

Significant aspects and features of the present invention include a member with extremely small holes of very minute size, such as in the order of angstroms across the cross-sectional area of the member. The small holes in the member have significant medical applications, as well as scientific applications. One such medical application would be in an intracorneal lens in providing for the passing of nutrients through the member, which would be formed as a lens, but yet being so small that an individual would not be able to see the holes.

Another significant aspect and feature of the present invention is that it allows to be placed in a predetermined, geometric configuration, which remains consistent throughout the member.

A further significant aspect and feature of the present invention is the use of polymethylmethacrylate, polysulfone or like material as the base material, and use of acrylic, styrene, ethyl cellulose, or the like as the filler material. Both the base and the filler material have similar drawing capabilities, thus enabling a consistency of hole size and placement in the base material during the production of the member. The filler material is then removed by chemical or physical action from the finished member. Any suitable material can be utilized as appropriately selected.

Still another significant aspect and feature of the present invention is the ribbon clamping fixture, which in the process of generating the member material, allows for the predetermined placement of strands of member material, including strands of material with holes, for producing ribbons of member material.

And an additional significant aspect and feature of the present invention is the boule clamping fixture, which further enables the predetermined configuration of holes in the member by placement of ribbons of member material into the fixture to form a boule for subsequent drawing steps.

Having thus described the embodiments of the present invention, it is the principal object to provide a member with extremely small holes which are cleanly and consistently configured in the member material to support medical applications, such as for the use of an intraocular lens or a medical filter, or the like.

Another object of the present invention is that the number of holes and the configuration of the holes in the member can be predetermined, allowing for any necessary variation of the number of holes in the member material for a variety of medical purposes.

An additional object of the present invention is the use of polymethylmethacrylate, polysulfone or like material as the base material, and use of a soluble filler material such as acrylic, other polymers, organic materials, metals, or the like. The filler material, upon cutting the member of a particular use, can then be removed through use of a solvent in a dissolving and washing process. The use of two materials with the same or similar drawing characteristics maintains proper hole size and consistency in production of the member depending upon the particular material selected.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein.

DESCRIPTION OF THE PREFERRED EMBODIMENTS

Figure 1:
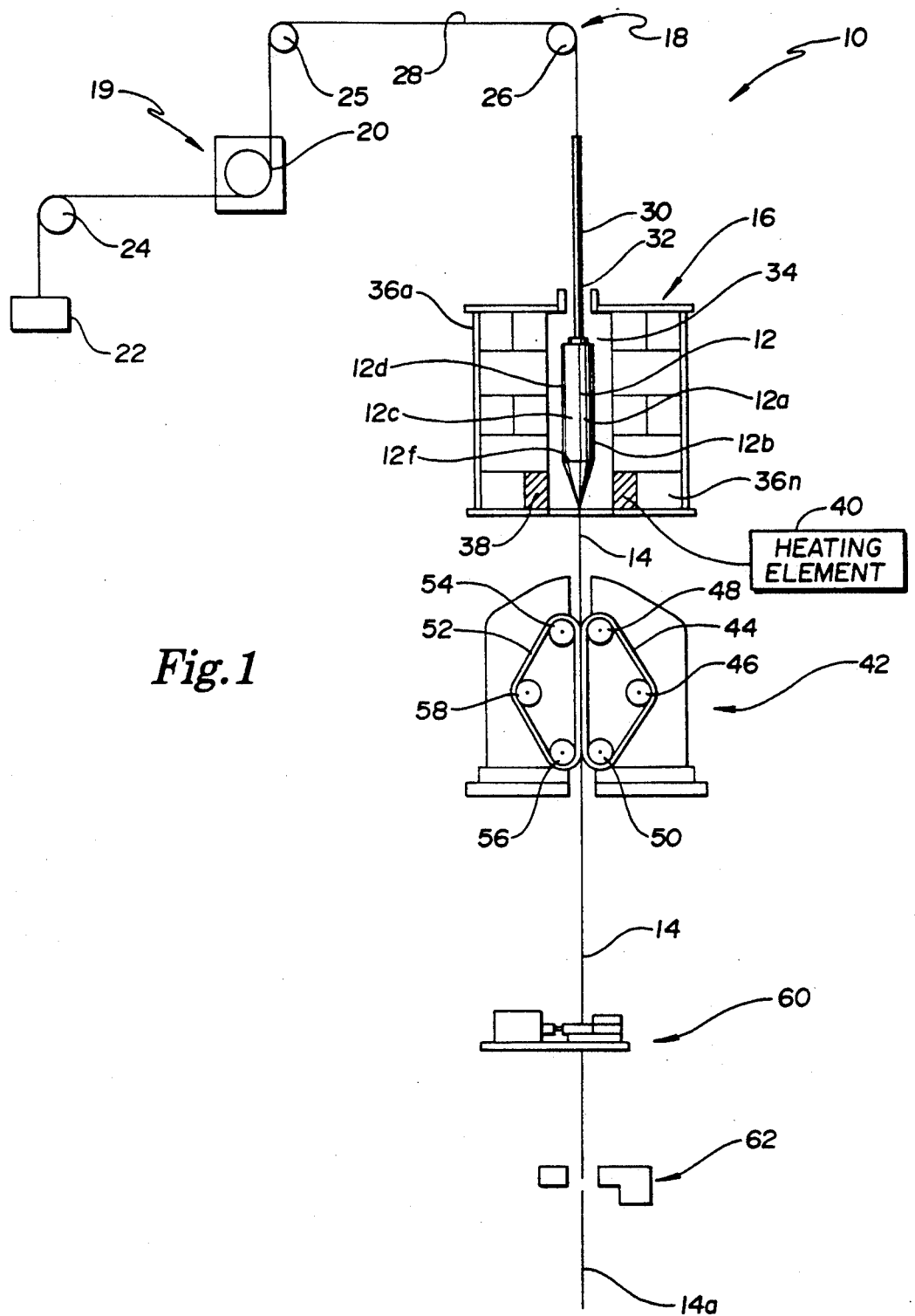
FIG. 1 illustrates an overview of the fenestrated boule drawing process.

FIG. 1 illustrates a perspective overview of the fenestrated boule drawing process 10. A large square first generation boule 12 with four sides 12a-12d, a flat top 12c and flat bottom 12f which is drawn to a narrow strand member 14 of either sold base material or solid material with a hole and a soluble filler material, is lowered in an oven 16. Both the base material and the soluble filler material have the same drawing characteristics to that as the first generation boule 12 is heated, the material can be drawn and pulled to form a first generation strand 14 of reduced cross-sectional area as a square. As the material is pulled, the hole is reduced. Other members of the process include a boule lowering chain system 18 including a adjustable speed motorized reduction gearbox sprocket 20 for regulation of the boule lowering speed, a counter weight 22, idler sprockets 24, 25 and 26, and a chain 28 connected to a boule 20 holder 30 and in engagement with idler sprockets 24-26 and the gearbox sprocket 20. The oven 16 includes an upper orifice 32 for accommodation of the boule holder 30, a cavity 34 surrounded by a plurality of bricks 36a-36n, an aluminum heat conductor member 38 aligned with the cavity 34 and secured to an external heating element 40. A strand puller 42 includes a driven belt 44 about a drive pulley 46 and idler pulleys 48 and 50. A similar driven belt 52 opposes the driven belt 44 about idler pulleys 54 and 56 and a spring loaded drive pulley 58. The opposing driven belts 44 and 52 rotate in an opposite direction. The strand 14 is sandwiched between the moving driven belts 44 and 52. The speed of the belts 44 and 52 is controllable to effect the tension and size of the strand 14 as it is drawn from the heated boule 12 in the oven 16. The strand 14 is sent through a pneumatically powered chopper 60 and electric eye system 62 which measures and chops the strand 14 to any desired length such as illustrated by a cut strand member 14a.

Figure 2:
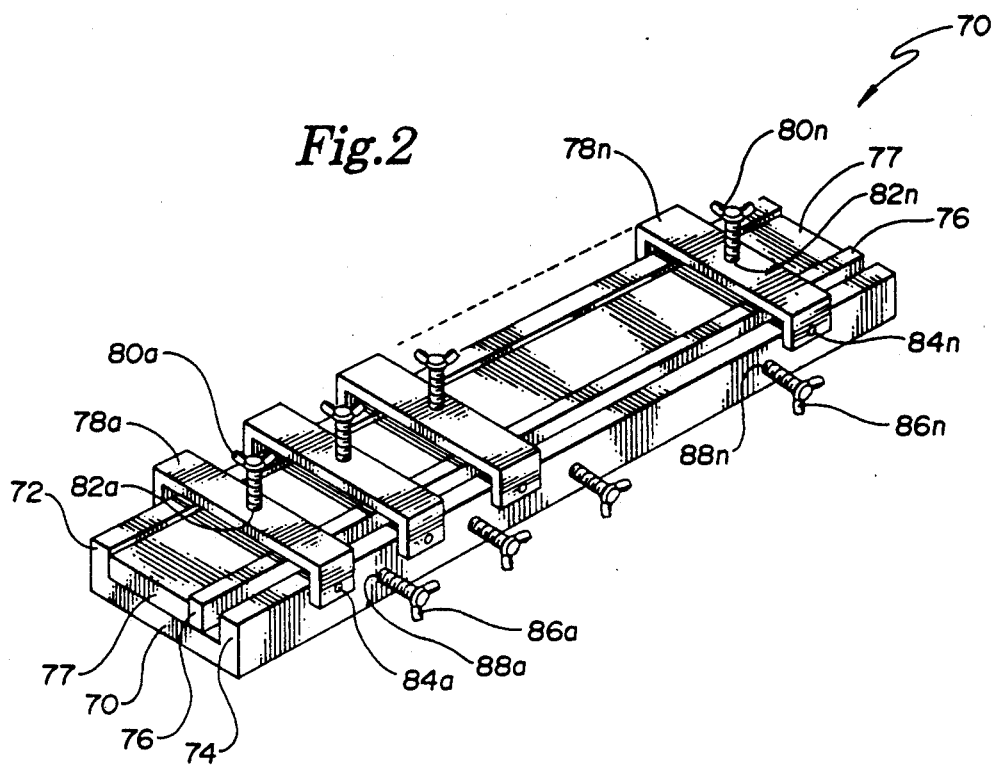
FIG. 2 illustrates a perspective view of the ribbon clamping fixture.

FIG. 2 illustrates a perspective view of the ribbon clamping fixture 70. The U-shaped ribbon clamping fixture includes a horizontal bottom member, a vertically aligned left edge member 72 and a vertically aligned right edge member 74 each of which extends vertically from the ribbon clamping fixture 70 and runs along the lengths of the right and left sides of the fixture 70. There is a vertically aligned movable clamping plate 76 and a horizontally aligned clamping plate 77 which are used to clamp boules. Horizontal U-shaped clamp support structures 78a-78n are screwed to the right edge member 74 and the left edge member 72. Thumb screws 80a-80n are positioned through holes 82a-82n located in the horizontal clamp support structures 78a-78n and tightened against the horizontal clamping plate 77. The horizontal clamping plate 77 is illustrated lying on the bottom of the "U" between left edge member 72 and the vertical clamping plate 76. Thumb screws 86a-86n align in holes 88a-88n and extend through the right edge member 74 to tighten against and along the vertical clamping plate 76. The horizontal clamp support structures 78a-78n, the thumb screws 84a-84n which fasten the horizontal clamping support structures 78a-78n to the main fixture, the top thumb screws 80a-80n, the side thumb screws 86a-86n allow for tightening and loosening the clamping plates 76 and 77 against a plurality of strands and are removable for insertion of strands of member material into the fixture 70.

Figure 3:
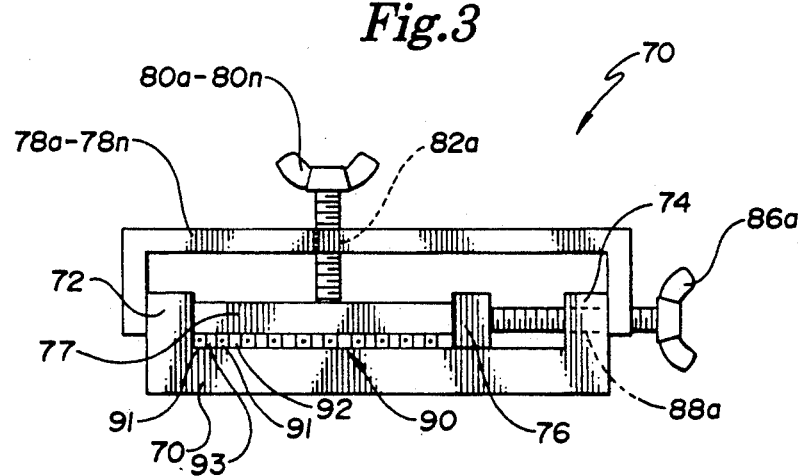
FIG. 3 illustrates an end view of the ribbon clamping fixture.
Figure 4:
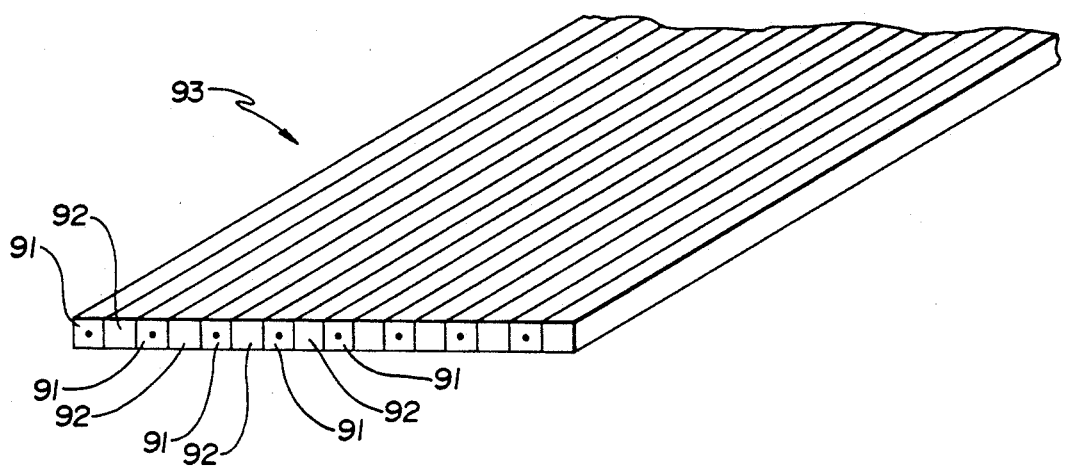
FIG. 4 illustrates a perspective view of a filled ribbon.

FIG. 3 illustrates an end view of the ribbon clamping fixture 70, further illustrating the horizontal clamping plate 77, the horizontal clamping support structures 78a-78n, the thumb screws 80a-80n, the clamping fixture 70, the right edge member 74 and the left edge member 72. This view also illustrates the vertical clamping plate 76 for side pressure, and thumb screws 86a-86n for adjustable vertical clamping plate 76 on a row 90. A single row 90 of filled strands 91 and solid strands 92 in a repetitive pattern of pulled boule material are placed side by side in a pattern as illustrated in the ribbon clamping fixture 70 in a side-by-side fashion. The horizontal clamping plate 77 provides downward pressure, and the vertical clamping plate 76 provides side pressure to keep the alternating plurality of strands 91 and 92 in place. The ribbon 93 is further illustrated and described in FIG. 4. As the boule strands 91 and 92 are baked in the process, they soften to form a single ribbon 93 as illustrated in FIG. 4. For purposes of illustration in FIG. 4 the vertical lines between the filled strands 91 and solid strand 92 are shown even though the ribbon 93 is a homogeneous member. The strands are not baked at a temperature hot enough or a time long enough to distort the holes in the strands. When the ribbon 93 cools, the ends are cut flush to form a trimmed boule ribbon as illustrated in FIG. 4.

Figure 4A:
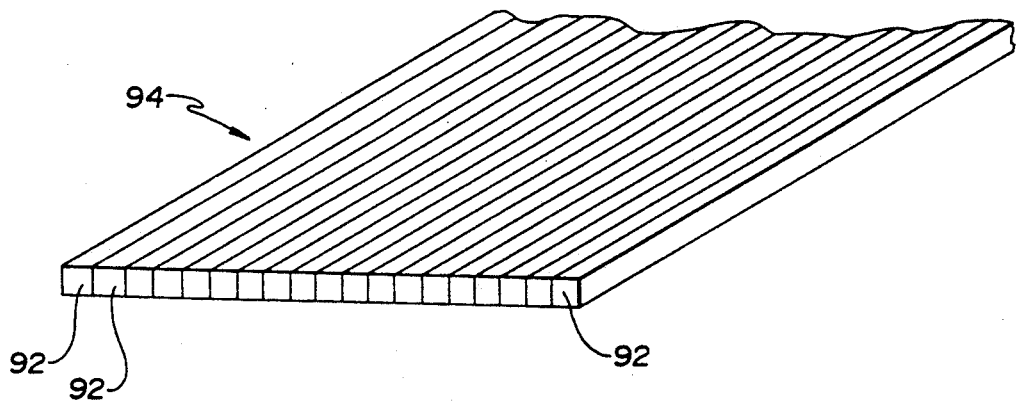
FIG. 4A illustrates a perspective view of an unfilled ribbon.
Figure 5:
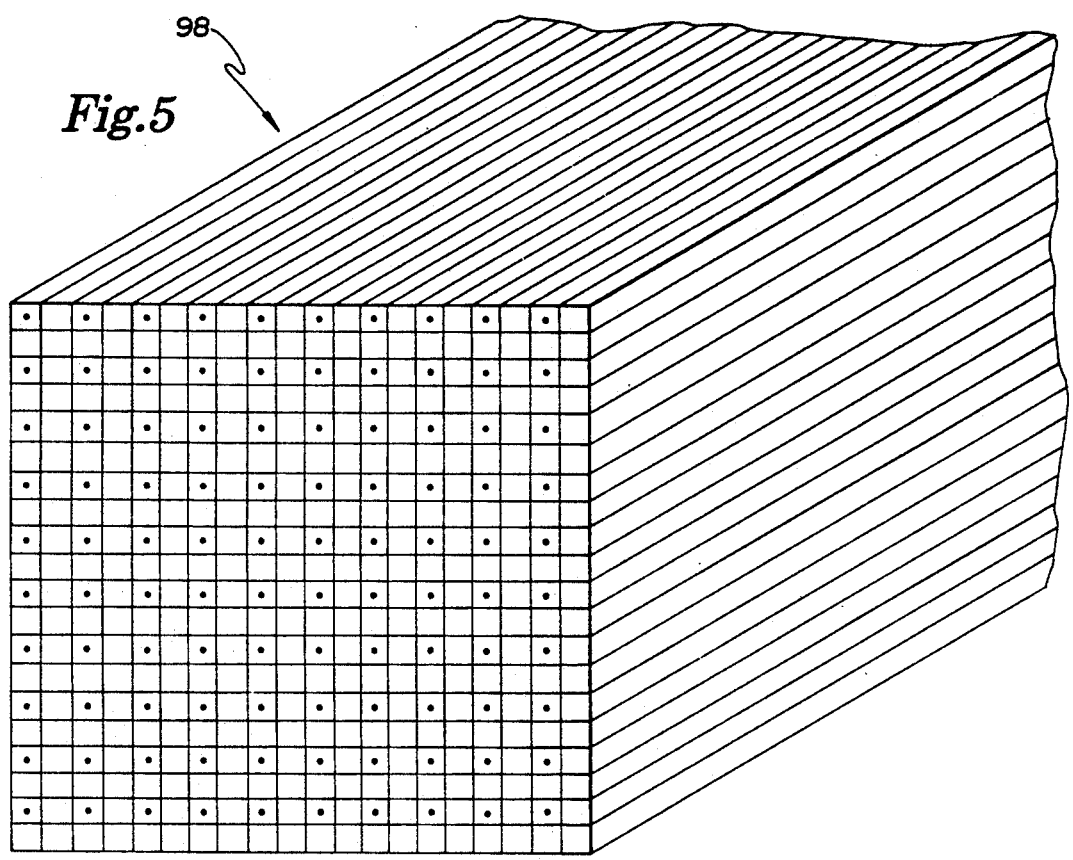
FIG. 5 illustrates a perspective view of a second generation boule prior to clamping and baking.

FIG. 4 illustrates a perspective view of a homogeneous ribbon 93 where all numerals correspond to those elements previously described. It will be appreciated that another homogeneous ribbon 94, as illustrated in FIG. 4A, is formed by employing a continuous row of solid unfilled strands 92 and clamping and baking them as described in FIG. 3. This process vertically alternates the filled strands when the ribbons 93 and 94 are stacked as illustrated in FIG. 5. As in FIG. 3, vertical lines are still shown in the rows 93 and 94 for purposes of illustration even though the alternating rows 93 and 94 are homogeneous members.

FIG. 5 illustrates homogeneous ribbons 93 and 94 arranged in an alternating fashion to form an unprocessed second generation boule 98 which is subsequently placed in a boule clamping fixture to form a second generation which after clamping and baking, forms a processed second generation boule 118.

Figure 6:
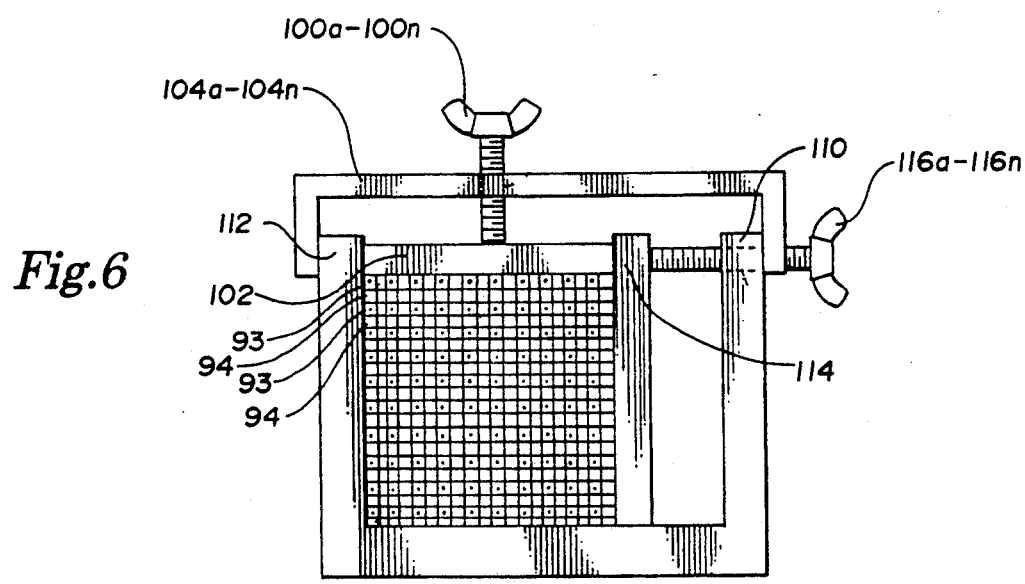
FIG. 6 illustrates an end view of the second generation boule in a boule clamp.

FIG. 6 illustrates an end view of the boule clamping fixture 100 further illustrating the clamping plate 102, the thumb screw support structures 104a-104n, the thumb screws 106a-106n, the horizontal bottom plate member 108, the right edge member 110 and the left edge member 112. This view also illustrates the sliding plate member 114 for side pressure and thumb screws 116a-166n for adjustable slide plate pressure on the unprocessed second generation boule 98. A column of ribbon material including alternating ribbons 93 and 94 is placed in the boule clamping fixture 100 so that the clamping plate 102 provides downward pressure, and the sliding plate member 114 provides side pressure to keep the ribbons 93 and 94 compressed and in place. As the ribbons of the unprocessed second generation boule 98 are baked, they soften to form a single homogeneous processed second generation boule 118 although they are not baked at a temperature hot enough or a time long enough to distort the holes in the ribbons. When the homogeneous processed second generation boule 118 cools, the ends are cut flush to form a trimmed homogeneous processed second generation boule 118 as illustrated in FIG. 7.

Figure 7:
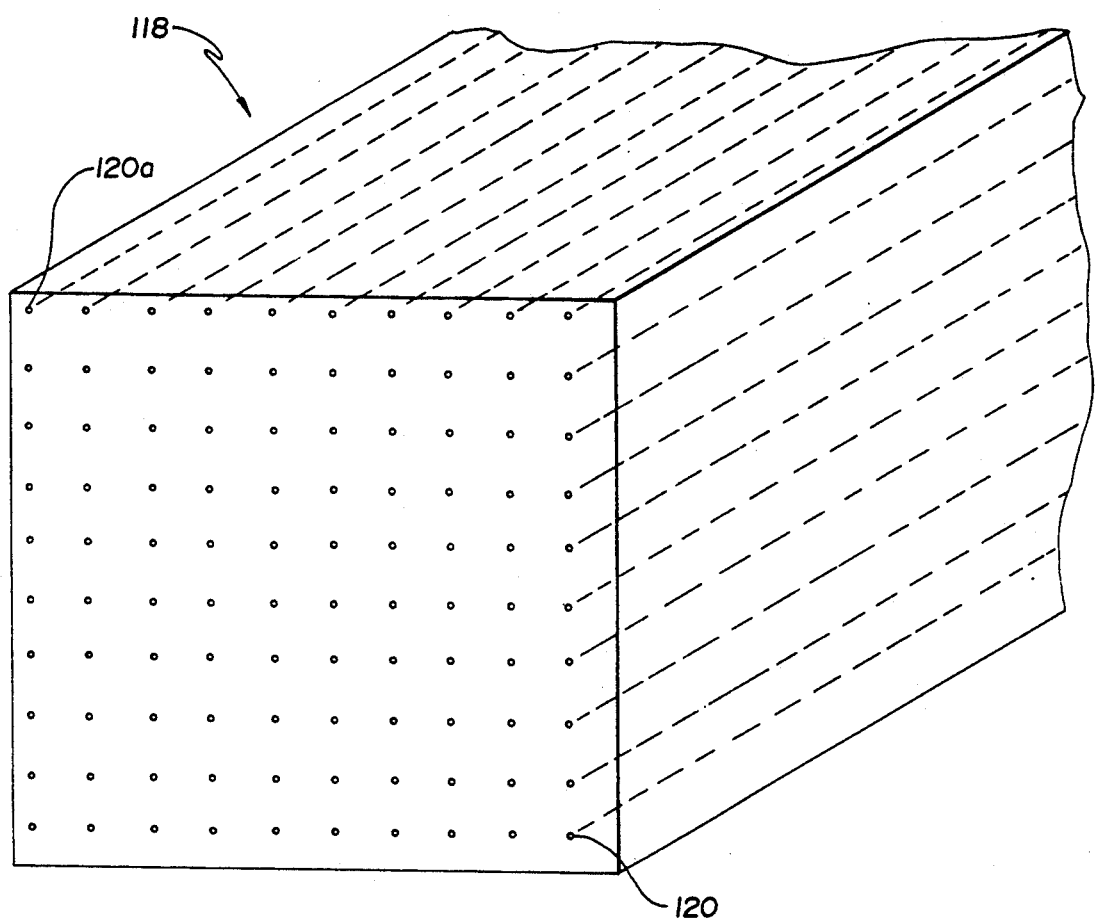
FIG. 7 illustrates a processed second generation boule formed from first generation strand ribbons.

FIG. 7 illustrates a perspective view of a homogeneous processed second generation boule 118 where all numerals correspond to those elements previously described and where the boule 118 was compressed and baked. This homogeneous processed second generation boule 118 has been formed of approximately 400 strands of the first generation strands or boule and processed to form a solid processed second generation boule 118 with a plurality of approximately 100 filled holes 120a-120n spaced about its cross section and extending the length of the boule 118.

MODE OF OPERATION

Figure 8:
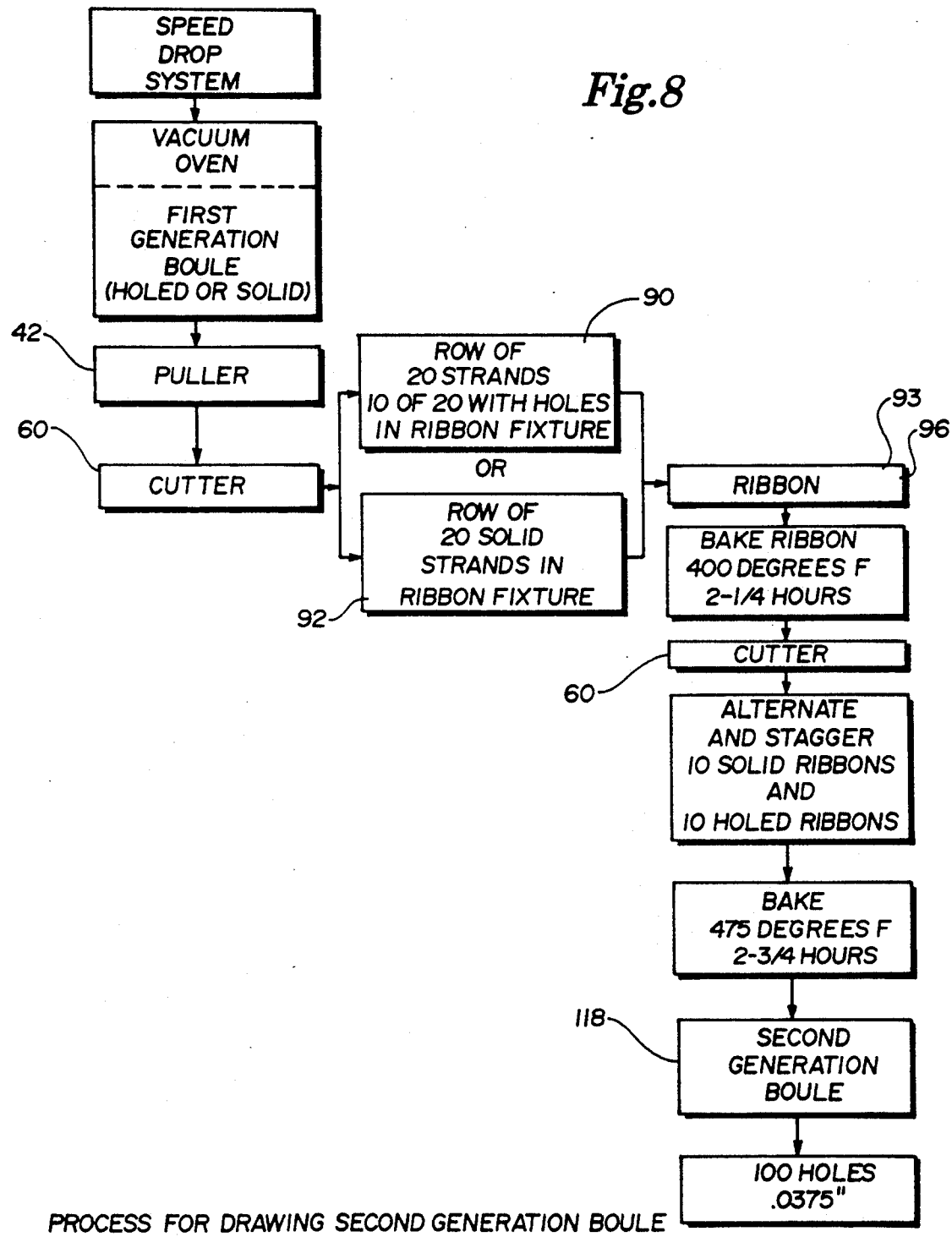
FIG. 8 illustrates a block diagram of the drawing procedure for generating a second generation boule; and, FIG. 9 illustrates a block diagram of the repetitive drawing procedure for generating a third or fourth generation boule.

FIGS. 8 and 9 provide a step-by-step flow chart generating a member with holes through a series of repetitive drawings, as illustrated in FIG. 1. By way of example and for purposes of illustration only and not to be construed as limiting of the present invention, the process for generating a member with holes begins with a first generation boule. A first generation boule is either of solid base material, such as polymethylmethacrylate, polysulfone, or the like, or base material with a hole and a soluble filler material, such as acrylic, styrene, ethyl cellulose, or the like to support the holes during drawing process. First generation solid boules are formed by extruding base material into square molds. First generation boules with holes are formed by installing a rod (tapered and Teflon coated) into the center of the mold, removing it, inserting a rod of filler material through the boule, flush cutting the ends of the boule, shallow drilling and tapping the bottom end of the boule, and installing an electrical conduit plug to prevent the flowing out of the filler material when placed in the heating oven.

A first generation boule 12 is positioned in a heating oven 16 via a chain 28 which is controlled and balanced by a counterweight 22, a motorized gearbox sprocket 20 with adjustable speed to regulate the drop of the boule into the oven, and idler sprockets 24-26 for both vertical and horizontal control of the chain 28 as it lowers the boule 12 into the oven 16. A boule holder 30 is attached to the boule and chain 28 for lowering it directly into the oven.

The first generation boule 12 is suspended in the oven 16 on the boule holder 30 which passes through a small orifice 32 in the top of the oven 16. The oven 16 is lined with insulating bricks 36a-36n, and at the center of the oven is square vertical cavity 34 for the boule 12. At the bottom of the oven is a conductor member 38 with a square hole 33 in the center which incorporates an external heating element 40 clamped to the outside of the oven to form a heating band around the bottom of the boule.

As the bottom end of the boule is heated, it drops down and is pulled by a strand puller 42 consisting of an opposing, counter-rotating, continuous belt system including belts 44 and 52. This strand puller 42 serves two main functions: the puller speed, in conjunction with the temperature of the oven, are adjustable to control the strand cross-sectional area, and to control of the position of the boule in the oven as it is used by the puller.

A speed drop system 19 is comprised of chain 28, counterweight 22, gearbox sprocket 20, idler pulleys 24-26, boule holder 30, and the strand puller 42.

Mounted under the puller is a pneumatic chopper which automatically cuts the pulled strands 14 into 13" lengths. An electronic eye 2 underneath the chopper controls the chopper 60 and allows adjustment of strand length. As a strand 14 is pulled, the member material retains its square shape and has a reduced cross-sectional area.

Strands 14 from first generation boule are placed side-by-side into the ribbon clamping fixture 70. Hole density of a ribbon, and the succeeding boule is controlled by the placement of alternating both vertically and horizontally, two types of ribbons are generated: one using only solid strands, and one using alternating holey and solid strands. Twenty strands are held firmly in place, flat and side-by-side in the ribbon clamping fixture by both vertical and horizontal clamps. The loaded fixtures are baked in an oven at appropriate temperatures to the materials being formed. The temperature and length of heating allows proper softening of the polysulfone, or like material, so that strands adhere to become one piece, although it does not allow distortion of the filled holes. After the ribbon fixtures are cooled, the ribbons are removed and ragged ends are trimmed to produce a 12-inch long ribbon.

Ribbons are then placed in the boule clamping fixture 100. To produce a second generation boule 118 with both vertical and horizontal alternating holes, ribbons are placed in the boule in the following manner: one solid ribbon, one holey ribbon, one solid ribbon, one holey ribbon, etc. Ribbons with holes are offset with each other for balanced symmetry. A total of twenty ribbons are placed in the boule clamping fixture at this time and the boule is clamped and baked for an appropriate time, temperature and pressure. When the second generation boule has cooled, it is removed from the boule clamping fixture, and the ragged ends are trimmed to produce a boule of length 11 inches. This second generation boule consists of 400 strands from the first generation boule, 100 of which have holes. These holes are now approximately 0.0375" in diameter.

FIG. 8 illustrates a step-by-step view of the repetitive process for generating a fourth generation boule. The second generation boule is placed in the oven and the whole process is repeated. As the material softens, it is again pulled and cut into 10 inch lengths. Twenty strands are placed in the ribbon clamping fixture. However, since at this point all the strands are similar with 100 holes, alternating solid and holey strands in the ribbon clamping fixture and boule clamping fixture is no longer necessary. Twenty ribbons are placed in the boule clamping fixture to generate a third generation boule. When the third generation boule is cooled, it will consist of 400 strands from the second generation boule, each with 100 holes, for a total of 40,000 holes, and the hole size has been pulled to 0.001875". To create a fourth generation boule, the entire process is repeated again, producing a boule containing 1,600,000 holes of size (approximate) 0.00009375".

This fourth generation boule is then pulled so that the strand cross section is 0.250" square; it will contain 1,600,000 holes, but they are now reduced to size 0.000015625", or 0.4 micron. From this, 6 millimeter diameter round stock can be machined from the square stock, which is then cut into 5 millimeter long buttons to be lathe cut for the actual lenses. The filler material is dissolved from the member using a solvent, leaving a lense with infinitesimal small, predetermined and consistently placed holes.

The boule can be a composite of one or more materials, and one or more of those materials can be soluble for removal at a later time. Chemicals, electrostatics or other processes can be used to dissolve out the soluble materials. The soluble materials can also be replaced by other materials for purposes of machining an article, such as a filter or an optic by way of example and for purposes of illustration only and not to be construed as limiting of the present invention. The boule can be a composite of nonsoluble materials with different physical properties, such as refractive index. The boule can also be a composite of both soluble and nonsoluble materials having discrete areas of concentration, and also discrete areas where the soluble and nonsoluble materials are mixed. The optics which can be created can be intraocular lenses, intracorneal lenses or contact lenses image sections of pies, circles, or any other geometrical discrete shapes. The filters can be filters requiring small holes such as in medical applications, particularly blood filtering applications. The holes in the lenses can be of such a size, such as 1 angstrom to 12 mm for the passage of nutrients and fluids through the lens, particularly intracorneal lenses or contact lenses.

Various modifications can be made to the present application without departing from the apparent scope hereof.

I claim:
1. A process of drawing a boule for use in the production of optics comprising the steps of:
 (a) forming a boule of a material substantially insoluble in a predetermined solvent, said material selected from the group consisting of polymethylmethacrylate and polysulfone, the boule having a plurality of holes therethrough;
 (b) filling at least one hole in said boule with at least one material substantially soluble in said predetermined solvent, said material selected from the group consisting of an acrylic polymer, a styrene polymer and ethyl cellulose, to create a composite material;
 (c) drawing said boule to form a smaller diameter boule;
 (d) cutting a plurality of smaller diameter boules into short sections;
 (e) laminating said short sections to obtain a second generation boule;
 (f) repeating steps (c), (d) and (e) a plurality of times to reduce the size of he filled holes; and
 (g) then dissolving he substantially soluble material in said predetermined solvent and washing the boule, thereby producing a drawn boule having a plurality of holes of reduced size therethrough.

2. A continuous process of drawing a boule for the production of composite materials for optics and filters, the process comprising the steps of:
 (a) forming a boule having longitudinal holes therein;
 (b) filling said longitudinal holes in said boule with a material substantially soluble in a predetermined solvent;
 (c) drawing sad boule to form a smaller diameter boule;
 (d) cutting a plurality of smaller diameter boules into short sections;
 (e) laminating said short sections to obtain a second generation boule;
 (f) repeating steps (c), (d) and (e) a plurality of times to create a redrawn composite having filled holes of a reduced size;
 (g) cutting and machining redrawn composites to form optics or filters;
 (h) dissolving the substantially soluble material in said predetermined solvent and washing the redrawn composite, thereby producing a redrawn composite having holes, slots or voids of reduced size therethrough; and
 (i) reimpregnating said holes, slots or voids of reduced size to facilitate machining.

* * * * *